(12) United States Patent
Smith et al.

(10) Patent No.: US 9,335,305 B2
(45) Date of Patent: May 10, 2016

(54) ULTRASONIC MEASUREMENT

(75) Inventors: Oliver Smith, University Heights, OH (US); Michael R. Sutton, Matlock (GB); Mitchell Peplow, Matlock (GB)

(73) Assignee: The Lubrizol Corporation, Wickliffe, OH (US)

( * ) Notice: Subject to any disclaimer, the term of this patent is extended or adjusted under 35 U.S.C. 154(b) by 513 days.

(21) Appl. No.: 13/977,986

(22) PCT Filed: Jan. 3, 2012

(86) PCT No.: PCT/US2012/020047
§ 371 (c)(1),
(2), (4) Date: Oct. 7, 2013

(87) PCT Pub. No.: WO2012/094298
PCT Pub. Date: Jul. 12, 2012

(65) Prior Publication Data
US 2014/0020468 A1    Jan. 23, 2014

Related U.S. Application Data

(60) Provisional application No. 61/430,229, filed on Jan. 6, 2011.

(51) Int. Cl.
*G01N 29/07*    (2006.01)
*G01N 29/34*    (2006.01)
(Continued)

(52) U.S. Cl.
CPC ............ *G01N 29/346* (2013.01); *B06B 1/0207* (2013.01); *G01N 29/07* (2013.01); *G01S 15/89* (2013.01); *A61B 8/58* (2013.01)

(58) Field of Classification Search
CPC .... B06B 1/0207; G01S 15/89; G01N 29/346; G01N 29/07; A61B 8/58
USPC ........................................... 73/597
See application file for complete search history.

(56) References Cited

U.S. PATENT DOCUMENTS 3,485,087 A * 12/1969 Brech .................... G01B 17/02
73/615
3,636,778 A *  1/1972 Huffstetler ............ G01B 17/00
73/622

(Continued)

FOREIGN PATENT DOCUMENTS

JP         62046282        2/1987

OTHER PUBLICATIONS

Written Opinion of corresponding International Application No. PCT/US2012/020047 dated May 15, 2012.
(Continued)

*Primary Examiner* — J M Saint Surin
(74) *Attorney, Agent, or Firm* — David M. Shold; Teresan W. Gilbert (57) ABSTRACT

Methods and apparatus relate to ultrasound measurement of a dimension such as the thickness (11) of an item (12) which may be worn over time by contact with an item (14). An ultrasonic transceiver (18) couples ultrasound into the item (12). Outgoing ultrasound i results in echos r returning to the transceiver (18). This allows calculation of time of flight to yield a value for the thickness (11). In the examples prescribed, the measurement is repeated a plurality of times in a specified period to extract a dimension from each received signal. Information extracted from the plurality of received signal is used to produce a single value indicative of the dimension of the item (12) over the specified period.

20 Claims, 5 Drawing Sheets

(51) Int. Cl.
    *B06B 1/02* (2006.01)
    *G01S 15/89* (2006.01)
    *A61B 8/00* (2006.01)

(56) References Cited

U.S. PATENT DOCUMENTS

| | | | | |
|---|---|---|---|---|
| 4,624,127 | A * | 11/1986 | Narushima | G01B 17/02 73/1.81 |
| 4,711,120 | A * | 12/1987 | Kwun | G01B 17/025 73/114.77 |
| 5,577,230 | A * | 11/1996 | Argade | G06F 9/3812 710/123 |
| 7,246,522 | B1 | 7/2007 | Diaz | |
| 7,678,049 | B2 * | 3/2010 | Tsoref | A61B 5/107 600/437 |
| 8,146,431 | B2 * | 4/2012 | Yashan | G01N 27/87 73/597 |
| 2004/0045356 | A1 | 3/2004 | Dwyer | |
| 2007/0068605 | A1 | 3/2007 | Statnikov | |
| 2008/0289420 | A1 | 11/2008 | Cochran | |
| 2009/0030629 | A1 | 1/2009 | Lampe | |
| 2009/0143681 | A1 | 6/2009 | Jurvelin | |

OTHER PUBLICATIONS

Corresponding International Publication No. WO 2012/094298 A1 published Jul. 12, 2012.
Search Report of corresponding International Application No. PCT/US2012/020047 dated May 15, 2012.
English Abstract of JP 62046282, European Patent Office-Patent Abstracts of Japan (copyright 1987, JPO&Japio).

* cited by examiner

ULTRASONIC MEASUREMENT

The present invention relates to ultrasonic measurement, and particularly but not exclusively to apparatus and methods for ultrasonic measurement of dimension.

In many instances, it can be useful to determine the effects of wear on an item, or to find a point where significant wear is about to occur, for example to improve efficiency. For example, an item that has regular contact with another item when in use might change in dimension over time, as it is worn away by the contact. Wear may also occur without contact, for example, through corrosive wear. Determining the effects of wear on an item can be important in calculating the expected life of the item, so that the item can be replaced before it fails or causes damage. Understanding the effects of wear is particularly important in machine components such as vehicle engine components or bearings. Determining the effects of wear can also be useful in testing the performance of an associated component, such as a lubricant.

There are currently two main ways of measuring wear known to the applicants. The first method of measuring wear requires analysing the surface of the item in question before and after it has been subjected to the effects of wear, for example using a coordinate measuring system. This method is not ideal, as it requires wear to already have occurred. It is also not possible to detect changes in the wear pattern whilst the wear is occurring over time.

Another method of measuring wear is radionucleotide testing (RNT), also known as surface layer activation (SLA) or thin layer activation (TLA). This method includes irradiating the surface layer of an item. As wear occurs, irradiated metallic atoms are washed into lubricant, which is then circulated past a scintillation counter. The number of irradiated atoms detected is thus indicative of the rate of wear. This method is able to measure wear in close to real time, with only a short time lag due to the time taken for the metallic atoms to circulate. However, this method can only be used in controlled laboratory settings, due to the use of radiation. It is difficult to measure wear of multiple components simultaneously, due to the limited availability of radio isotopes, some of which have limited half lives. Furthermore, the measured wear rate often differs from the actual wear rate, as not all dislodged atoms are necessarily circulated.

According to a first aspect of the present invention there is provided a method of ultrasonic measurement, the method comprising the steps of:

transmitting an ultrasonic signal into an item, receiving an ultrasonic signal from the item, the received signal comprising a reflection of the transmitted signal from a boundary of the item, repeating the transmitting and receiving steps a plurality of times in a specified period, extracting from each received signal information indicative of a dimension of the item, and using information extracted from the plurality of received signals to produce a single value indicative of the dimension of the item over the specified period.

The steps need not necessarily occur in the order above, but might be executed in any suitable order.

The single value might be a value for the dimension of the item. The single value might be a time of flight value.

The item may comprise one or more of: metals, alloys, plastics, concrete, ceramics, coated materials and composite materials. When the item comprises a metal, the metal may be selected from steel, aluminium, copper, brass, tin, lead, bismuth, and alloys of the above. The item may comprise an aluminium oxide and/or an aluminium silicate.

The method may include the step of determining a time of flight value from the information extracted from a respective received ultrasonic signal. A set comprising a plurality of time of flight values may be produced. Each time of flight value in the set may correspond to a respective received signal.

Producing the value for dimension may comprise combining the plurality of time of flight values to produce a composite time of flight value, and may comprise using the composite time of flight value to determine the value for the dimension of the item.

Producing the composite time of flight value may comprise performing a statistical operation, such as taking an average of the time of flight values, such as a mean, median or trimmed mean (typically the mean).

Producing the composite time of flight value may comprise the step of producing a plurality of time of flight sub-values, and combining the time of flight sub-values to produce the composite time of flight value. Each time of flight sub-value may be produced from a sub-set of the time of flight values.

Producing the value for dimension may comprise producing a composite time of flight value from the information extracted from the plurality of received signals, the composite time of flight value being indicative of an average time of flight, and may comprise using the composite time of flight value to determine the value for the dimension of the item.

The transmitting and receiving steps may be repeated between 2 and 1,000,000 times over the specified period, which may be a second, or may be a fraction of a second, such as 0.2 seconds, or 0.5 seconds. The transmitting and receiving steps may be repeated between 2 and 450,000 times over the specified period, and may be repeated between 1000 and 100,000 times. Where the period is three seconds, the transmitting and receiving steps may be repeated 40,000 times. Where the period is 0.2 seconds the transmitting and receiving steps may be repeated 4005 times.

The above ranges may be appropriate where the item comprises a metal. Where the item comprises a non-metal, the number of transmitting and receiving steps may be the same, increased or reduced in dependence on the acoustic properties of the material. For example, the number of transmitting and receiving steps may be halved, or may be reduced to one third, one quarter, or one fifth of the above ranges.

The method may further comprise the step of repeating the method at intervals to produce a plurality of composite dimensional values. The intervals may be regular intervals, for example the method may be repeated once a minute, or once every two minutes, ten minutes, hour, etc. In one embodiment, the method may be employed wherein the item which is measured is subject to wear and said wear is evaluated by comparing the plurality of dimensional values.

The step of determining the time of flight value may comprise identifying a time at which a zero amplitude of the reflected signal occurred. The zero amplitude may comprise an intercept zero, for example, a zero following a peak amplitude. The zero may comprise a first intercept zero.

The receiving step may comprise receiving a first reflection of the transmitted signal. The receiving step may comprise receiving a higher order reflection, for example a second reflection, third reflection, or other multiple reflection.

The method may further include the step of measuring one or more temperatures within an item. The temperatures may be measured over the specified period. The method may include the step of adjusting the composite dimensional value (if necessary) to calibrate the value with respect to temperature.

According to a second aspect of the invention there is provided an apparatus for determining a dimension of an item, wherein the apparatus is operable to perform the method of the first aspect of the invention. The apparatus may be operable to perform any combination of the method steps referred to above with respect to the first aspect of the invention, in any suitable order.

The apparatus may comprise an ultrasonic transmitter operable to transmit an ultrasonic signal into an item and an ultrasonic receiver operable to receive an ultrasonic signal from an item. The ultrasonic transmitter and the ultrasonic receiver may together comprise an ultrasonic transceiver. The ultrasonic transceiver may be operable to produce either a broadband ultrasonic pulse, or an ultrasonic pulse having a frequency of between 1 and 100 MHz, for example 2 to 50 MHz, 3 to 50 MHz, or 5 to 20 MHz. The ultrasonic transceiver may comprise a frequency of substantially 20 MHz. The ultrasonic transceiver may comprise a frequency of substantially 10 MHz. The ultrasonic transceiver may comprise a piezoelectric transducer.

The apparatus may comprise a control system which is operable to supply an electrical signal to the ultrasonic transceiver to cause the ultrasonic transceiver to transmit the ultrasonic signal. The control system may be further operable to receive an electrical signal from the ultrasonic transceiver, the received electrical signal comprising information indicative of a dimension of the item.

The control system may be operable to cause the ultrasonic transceiver to transmit a plurality of ultrasonic signals in a specified period, and may be operable to receive a plurality of electrical signals from the ultrasonic transceiver in the specified period.

The control system may be operable to supply a voltage pulse to the ultrasonic transceiver. The control system may comprise a pulse generation module operable to supply the voltage pulse. The voltage pulse may be shaped, and may comprise a square wave, a triangle wave, or a sine wave, or part thereof. A wideband (multiple frequencies) wave can also be used to excite the transceiver. The wave may comprise a frequency of between 1 and 100 MHz, for example 2 to 50 MHz, 3 to 50 MHz, or 5 to 20 MHz. The wave may comprise a frequency of substantially 20 MHz. The wave may comprise a frequency of substantially 10 MHz.

The voltage pulse may have a peak amplitude of less than 200V, and may have a peak amplitude of between 2 and 100V, for example 5 and 20V. The voltage pulse may have a peak amplitude of approximately 10V.

The pulse generation module may comprise a pulse generator operable to generate an initial voltage pulse and an amplifier operable to amplify the initial voltage pulse to produce an amplified pulse. The pulse generation module may further comprise a signal blocker which is operable to shield the pulse generator from the amplified pulse. The signal blocker may comprise a field-effect transistor. The signal blocker may be synchronised with the amplifier, such that the signal blocker is operable only when the amplifier is transmitting the amplified pulse, and is not operable otherwise.

The ultrasonic transmitter and the ultrasonic receiver may be embodied separately to isolate the receiver from the excitation provided by the transmitter.

The control system may be operable to extract from the received ultrasonic signals information indicative of a dimension of the item, and may be operable to use the information extracted from the plurality of received signals to determine a single value for the dimension of the item over the specified period. The control system may be operable to determine a time of flight value for a respective electrical signal, and to combine a plurality of such time of flight values to produce a composite time of flight value. The control system may use the composite time of flight value to produce the dimensional value.

The apparatus may further include one or more temperature sensors, which may comprise one or more thermocouples. The control system may be operable to calibrate the value for dimension using a temperature measurement provided by the temperature sensor.

According to a third aspect of the invention there is provided an item comprising an apparatus in accordance with the second aspect of the invention. The item may be a machine such as a vehicle, or may be comprised within a machine such as a vehicle component (for example, an engine part).

The present invention will now be described, by way of example only, with reference to the accompanying drawings, in which.

Figure 1:
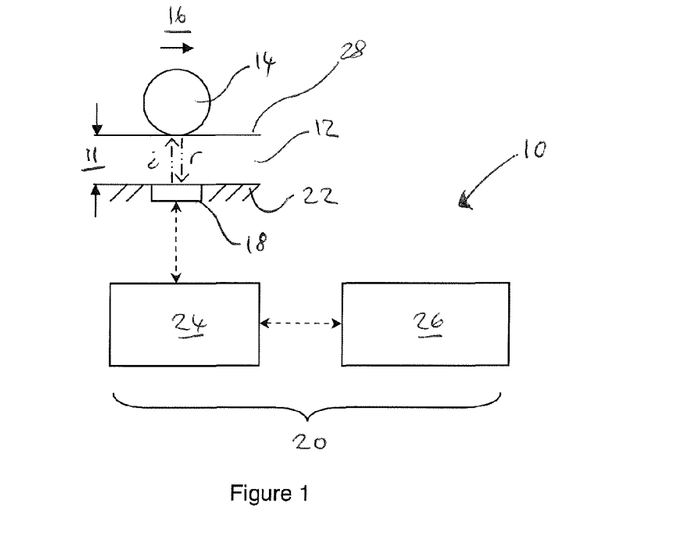
FIG. 1 is a schematic view of an apparatus for measuring a dimension of an item.

Referring firstly to FIG. 1, an apparatus 10 for measuring a dimension of an item 12 using ultrasound is shown.

Ultrasound refers to the portion of the sound frequency spectrum which is above human hearing, and typically is taken to include sounds having a frequency of greater than 20 kHz. Ultrasound pulses pass through solid bodies at a speed determined by their material properties. Ultrasound pulses are typically reflected from interfaces or boundaries when a change in acoustic properties occurs.

An ultrasonic signal which is reflected from a boundary includes information about that boundary. For example, information about the distance to the boundary can be determined by measuring the time taken for an ultrasonic pulse transmitted into an item to pass through an item to the boundary and return as a reflection. It is possible (knowing the speed of sound in the material from which the item is made) to calculate the distance traveled by the reflected wave from this measured time. That distance is indicative of a dimension of the item, and in particular the distance to the boundary. Where the boundary is a surface, the dimension is indicative of the thickness of the item.

Figure 2:
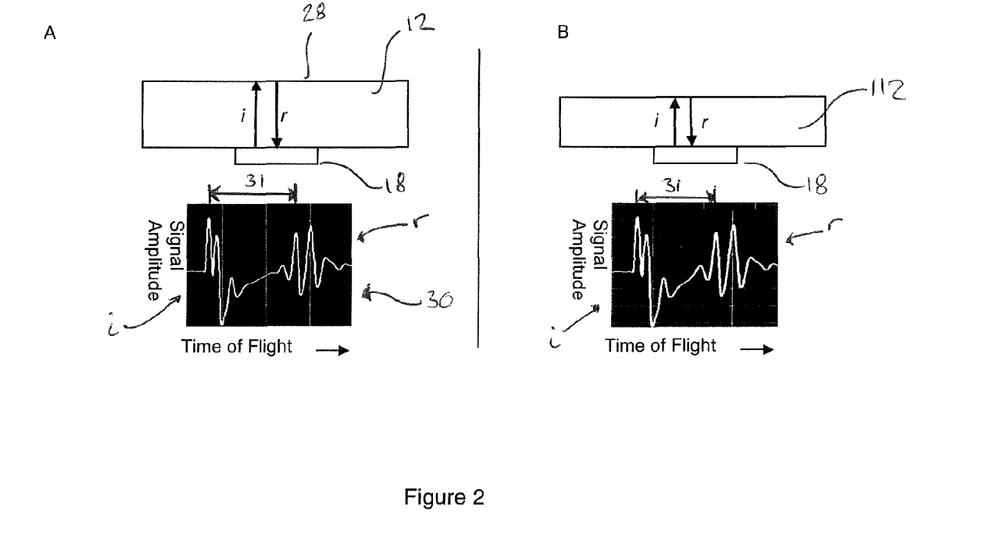
FIG. 2 illustrates schematically the difference between the time of flight in a first item (A) and a second item (B)

This method is illustrated more clearly in FIG. 2. FIG. 2A shows an ultrasonic transceiver 18 coupled to an item 12. When the transceiver 18 is excited by a suitable electrical pulse, the transceiver emits an ultrasonic signal i. That signal is transmitted through the item in a direction generally normal to the plane of the surface to which the transceiver is fixed. When the signal reaches a boundary, such as a test surface 28 of the item, at least a portion of the signal is reflected. The reflected signal r is detected at the ultrasonic transceiver 18 and converted to an electrical signal.

FIG. 2A also shows a graphical illustration 30 of the amplitude variations of the transmitted pulse i and the reflected pulse r over time. The reflected signal has a generally similar shape to the transmitted signal, but a reduced amplitude, as some signal energy is lost (due to attenuation, and because not all the signal will necessarily be reflected).

The time 31 between the transmitted pulse and the received pulse is the signal's 'time of flight'. This time of flight 31 is indicative of the distance traveled by the signal, which distance is equal to twice the thickness of the item.

FIG. 2B illustrates a similar situation to FIG. 2A, but with an item 112 which is thinner than the item 12 shown in FIG. 2A. In this example the item 112 is item 12 after it has experienced some wear. It will be seen that the time 31 between the outward i and reflected r pulses in FIG. 2B is less that the equivalent time in FIG. 2A, because the distance traveled is shorter.

One difficulty with measuring dimension, in particular measuring change in dimension, in real time to provide an indication of wear, is that dimension measurements necessarily include some degree of uncertainty.

As used herein, the term "uncertainty" (also referred to as U) means a single measurement (X) of thickness is a value such that, X±U forms a 95% confidence interval for the true, underlying, mean value of the thickness of the sample. Let s be the standard deviation that would be obtained from a large sample of repeated thickness measurements of the same sample in a steady state (no wear occurring) at a constant temperature within a short period of time. It is assumed that the sampling procedure is such that the measurements are not autocorrelated. Then the uncertainty is defined as 1.96·s.

It is also possible to define the uncertainty associated with a temperature-adjusted thickness measurement based on the standard deviation between measurements on the same sample with no wear occurring, at different temperatures, assuming a sampling procedure is chosen so that temperatures are randomly selected and measurements are independent. This uncertainty would be larger than that from a constant temperature as there will be uncertainty in the estimates of the parameters of the calibration equation.

The uncertainty is distinct from the repeatability of the method, as it deliberately does not take into account variation between runs, or due to sample preparation, but rather, is the uncertainty associated with a particular measurement at a particular time, due to short-term variation in the measurement.

The uncertainty for a wear measurement is defined as ½ the width of a 95% confidence interval for the difference between measurements on the same sample before and after wear has occurred, and is equal to $1.96 \cdot s \cdot \sqrt{2}$. The value of s used may be based on raw or temperature-adjusted thickness measurements as appropriate.

To provide a useful indication of wear it is necessary to be able to measure dimension to a very low uncertainty, so that small changes in thickness (i.e. small amounts of wear) can be detected. It is typically desirable to be able to detect wear with an uncertainty of less than 1 μm, and preferably 10 nm or less. For example, an uncertainty of between 1 and 5 nm may be desirable, as measured over a time period of 1 second.

To determine a distance to this degree of accuracy would require measurement of the time of flight of an ultrasonic pulse to within picoseconds. This is currently both difficult and expensive, and is impractical in a non-laboratory environment.

We have found that, rather than producing a dimensional measurement from a single very accurate measurement of time of flight, it is possible for a low uncertainty dimensional measurement to be produced from a plurality of less accurate time of flight measurements.

The apparatus 10 shown in FIG. 1 is operable to measure multiple values of the time of flight in quick succession over a specified period (such as 1 second). Those multiple values are statistically combined to produce a composite time of flight value which is used to determine a value for the dimension of the item in that specified period.

In the example shown, the item under test 12 is in contact with a second item 14, and relative motion occurs between the two items, indicated in FIG. 1 by arrow 16. Over time, the relative motion between the items 12 and 14 causes wear to both items. A lubricant such as an oil-based lubricant may be provided between the items to alter, and in particular reduce, the effects of wear.

The apparatus 10 includes two main components, namely an ultrasonic transceiver 18 and a control system 20. The ultrasonic transceiver takes the form of a piezoelectric transducer which is able to both transmit an ultrasonic pulse into the item under test 12 and receive an ultrasonic pulse from the item 12. The ultrasonic transducer is physically coupled to the item 12, for example by gluing the transducer to a surface 22 of the item, or by depositing piezoelectric crystals forming transducer in situ on the item.

The control system 20 is in communication with the ultrasonic transducer, and is operable to cause the ultrasonic transducer 18 to emit an ultrasonic signal. The control system 20 is also operable to interpret ultrasonic signals detected by the transducer.

The control system 20 includes a pulse generation module 24 and a controller module 26. The pulse generation module 24 is operable to generate an electrical pulse to excite the ultrasonic transducer in response to an instruction from the controller module 26. When excited by an electrical pulse, the ultrasonic transducer is caused to emit an ultrasonic pulse.

The pulse generation module 24 is further operable to receive an electrical signal generated by the ultrasonic transducer. The electrical signal is generated when an ultrasonic wave is incident with the ultrasonic transducer. The pulse generation module is operable to communicate a received electrical signal to the controller module for interpretation and analysis.

Figure 7:
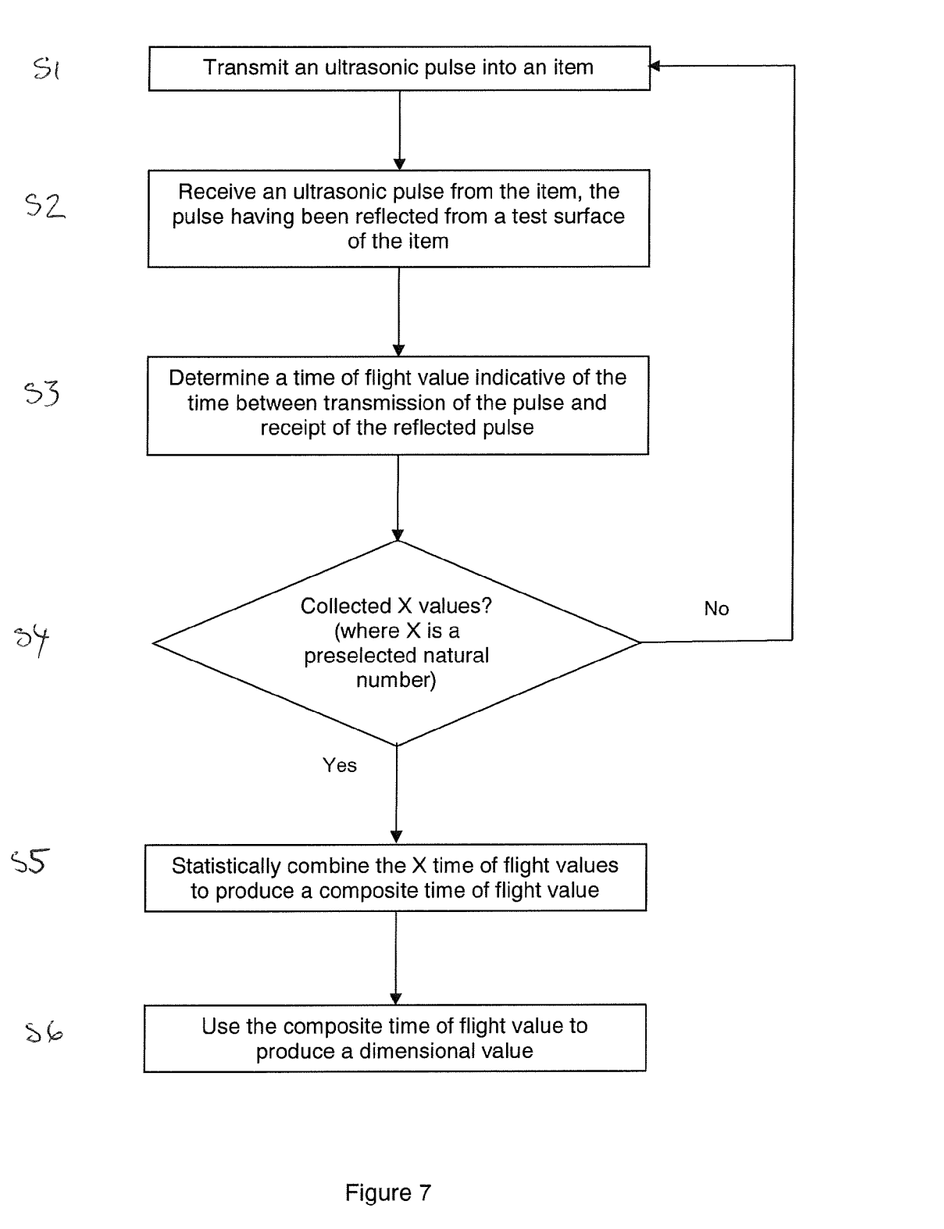
FIG. 7 is a flow chart depicting a method for measuring a dimension.

In use, the apparatus shown in FIG. 1 implements the method set out in FIG. 7 in order to determine a value for a dimension 11 of the item under test 12.

At step S1 an ultrasonic pulse is transmitted through the item 12 under test. In particular, the controller module causes pulse generation module to generate a voltage pulse, which in turn causes the ultrasonic transducer to generate an ultrasonic pulse. The ultrasonic pulse is transmitted into the item 12 because the ultrasonic transducer is coupled, and in this example permanently coupled, to the item.

The transmitted ultrasonic pulse is subsequently reflected from a test surface 28 of the item, and the reflected pulse is received in step S2. The reflected pulse is received at the same location from which the original pulse was transmitted, and in particular at the ultrasonic transducer from which the pulse originated. The ultrasonic pulse is converted to an electrical signal by the ultrasonic transceiver, which is forwarded to the controller module for interpretation. Both the received ultrasonic pulse and the converted electrical signal contain information about the distance to the surface.

At step S3 a time of flight of the pulse is determined from the electrical signal. Typically a single time of flight value can be determined to an uncertainty of ±1 μm, which is in general has too large an uncertainty for the purposes of quantifying wear. In the apparatus 10, the time of flight value is determined by the control system, and in particular the controller module, and saved in memory.

At step S4, the steps S1 to S3 are repeated until a sufficient number of time of flight values have been collected. Sufficient in this instance refers to enough data points to represent the thickness of the item to a desired uncertainty based on the variability of the ultrasonic measurement. This number is normally predetermined, but does not necessarily need to be. The number of repetitions may be any natural number greater than 1 (e.g. two, ten, one hundred, one thousand, ten thousand, one million, etc). In general, the larger the number of values collected the greater the accuracy that is achieved.

In the example apparatus 10 the control system is operable to cause the steps S1 to S3 to repeat a predetermined number of times. The control system stores the plurality of time of flight values which are determined in memory, until its memory comprises a set of time of flight values equal in number to the predetermined value.

Once the preselected number of values has been collected the method moves on to step S5. In step S5 the plurality of measured time of flight values are combined to produce a composite time of flight value. In the example method shown, a normal distribution of the values is used to statistically combine the values to determine the mean value. The standard deviation from the mean may also be used to calculate the standard error of the mean. Once the composite time of flight value has been produced the measured individual time of flight values may be discarded (e.g. deleted from the memory) if required.

At step S6 the composite time of flight value is used to produce a single dimensional value, which is indicative of the average distance traveled by each of the ultrasonic pulses over the period in which the plurality of measurements took place. The time period selected is short enough such that even in conditions of extreme wear the physical distance is unlikely to change significantly (such as less than 1 nm). For example, the plurality of measurements might be made within the same second.

Combining the results of many measurements in this way results in a less uncertain value for the dimension under test, as the effects of noise are cancelled out in the averaging step.

Such a method and system can be used to measure a dimension of an item, such as its thickness, in real time. We have found it possible to measure dimension with an uncertainty of less than 10 nm (typically 1-5 nm or 2-3 nm) using a set of approximately 40,000 time of flight values taken over a three second period.

Multiple dimensional values can be produced if the method set out in FIG. 7 is repeated at intervals, e.g. regular intervals such as once every 0.2 seconds, once a second, once a minute, or once every ten minutes. The plurality of dimensional values can be stored in memory of the controller module and/or transmitted to a remote location for storage and/or analysis, as appropriate, thus providing an accurate indication of the rate of wear over time, including changes in wear rate.

The described system and method is robust, and can be used in the field as well as in a laboratory. The system can measure extreme changes in thickness, and is not limited to measuring wear of a thin radioactive surface layer. The system can be used with any material through which an ultrasonic pulse can be transmitted, such as metal, resin and plastics. Furthermore, any number of ultrasonic transducers might be provided in one system 10, or multiple systems 10 could be used in parallel, permitting multiple measurements to be taken simultaneously, on a plurality of different components if required.

When implementing the method described herein in a practical system we have found that a number of factors can affect measurement accuracy, and these are discussed in more detail below.

Ultrasonic Pulse Generation

If the transmitted ultrasound pulse has too low an amplitude, the reflected return signal may be difficult to detect over background noise, due to attenuation losses and the fact that not all the signal is necessarily reflected. A low amplitude transmitted pulse is particularly problematic if the system is used in a wet environment (e.g. where a liquid such as an oil or other lubricant is present on the test surface).

In general, the stronger the outgoing signal, the stronger the corresponding reflected signal. However, we have found that emitting a high amplitude outgoing pulse does not necessarily give the best results, particularly where the reflected signal is detected by the same transducer which emitted the initial pulse, as in the example system described above.

After emission of a voltage pulse, a pulse generator typically experiences a period of 'relaxation' during which significant noise is generated. The higher the voltage pulse emitted the greater this amount noise, and the longer it takes to die away. If this relaxation period is too great, detection of the returning ultrasound pulse can be difficult, as the signal is likely to be lost in noise.

The excitation voltage of the pulse generation module has therefore been selected taking these opposing considerations into account. We have found that a suitable voltage is less than 200V, for example in the range 1-100V, and in particular in the range 3-20V. The sample system described below uses a voltage of 10V.

We have also found that good results are achieved when the voltage pulse generated (and hence the ultrasonic pulse) has a repeatable shape. Use of a repeatable pulse shape simplifies measuring time of flight repeatably, and also reduces the impact of noise on the composite time of flight value. In addition, if the pulse generation is repeatable (or at least any variations in generation are predictable and minimised) the system can be more easily calibrated in relation to temperature (more detail below).

A piezoelectric ultrasonic transducer can be excited by supplying a voltage pulse to the transducer. One way of generating such a voltage pulse is using a capacitor. Another way is using an operational amplifier. Both methods produce a reasonably repeatable pulse. However, the shape of the signal generated by an amplifier is typically more controllable than that generated by a capacitor, allowing generation of a specific shape of wave. In particular, using an amplifier enables generation of sine waves (for example by producing a voltage pulse shaped as a square wave, a triangular wave or a sine wave).

Ultrasonic transducers are generally optimised to function most effectively at a specified frequency, and so producing an excitation pulse in the form of a sine wave at or near this frequency of operation can be more efficient.

A third consideration in ultrasonic pulse generation relates to the frequency of the ultrasonic transceiver (and so the frequency of the ultrasonic pulse). In general, lower frequency signals have better transmission characteristics (e.g. reduced attenuation). However, we have found that higher frequency signals are easier to analyse in a repeatable way (discussed in more detail below). A suitable frequency might be selected from the range 1-100 MHz, and in particular the range 3-50 MHz. The system described above uses a frequency of 10 MHz, although frequencies of up to 30 MHz, e.g. MHz, have also been found to give good results.

Time of Flight Measurement

The time of flight of the reflected pulse can be measured by noting the time at which a predetermined feature on the reflected wave is received. This received time can be compared with the time at which the equivalent feature on the outgoing pulse was generated (which may either be measured or known) in order to determine the time of flight.

Figure 3:
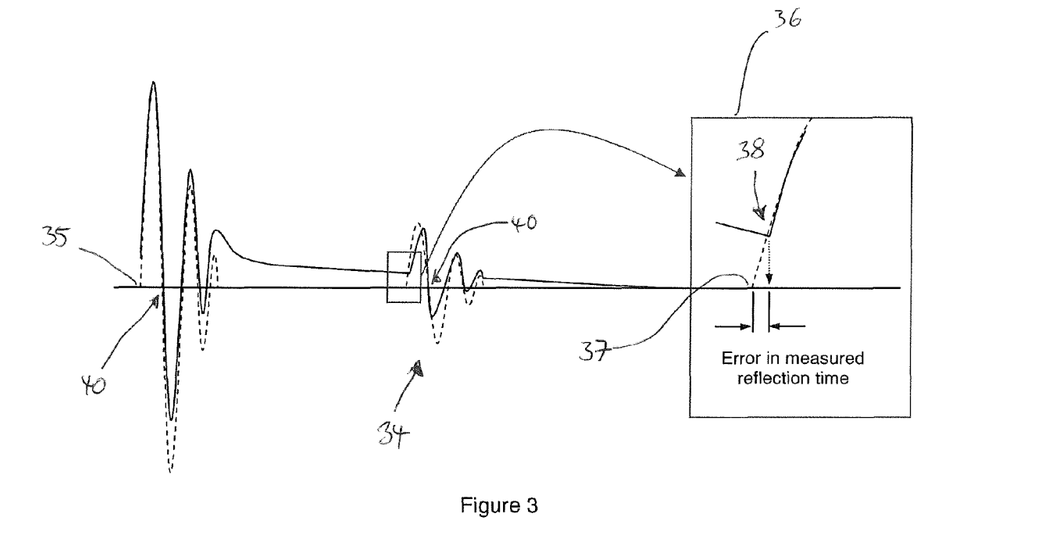
FIG. 3 schematically compares a signal that might have been generated by system including a capacitor bank and an ideal signal.

Selecting the feature on which to base the measurement requires a number of practical considerations. Typically, time of flight is calculated by measuring the time between the peak amplitude of the transmitted signal and the peak amplitude of the return signal. However, interactions with the test surface can distort the shape of the reflected signal, resulting in movement of the peak of the measured reflected signal from its expected location as compared with a simulated reflected peak. This phenomenon is shown in FIG. 3, where at 34 the change in amplitude over time of a simulated or 'ideal' reflection is shown in broken lines, overlaid for comparison with a measured reflection in solid lines. It will be seen that the shape of the measured reflection is distorted with respect to the ideal signal, due to noise. In particular, the peak amplitude has changed, as has the time at which that peak occurs as measured on the x-axis.

The distortions in the shape of the reflected peak are not necessarily consistent from one measurement to the next (for example, surface contaminants may disperse or increase over time). When measuring peak to peak, these amplitude variations can introduce perceived changes in time of flight which do not correspond to physical changes in dimension, resulting in inaccuracy.

We have found that a better approach is to compare time between two points of zero amplitude. However, this approach also has complications, illustrated in FIGS. 3 and 4.

Figure 4:
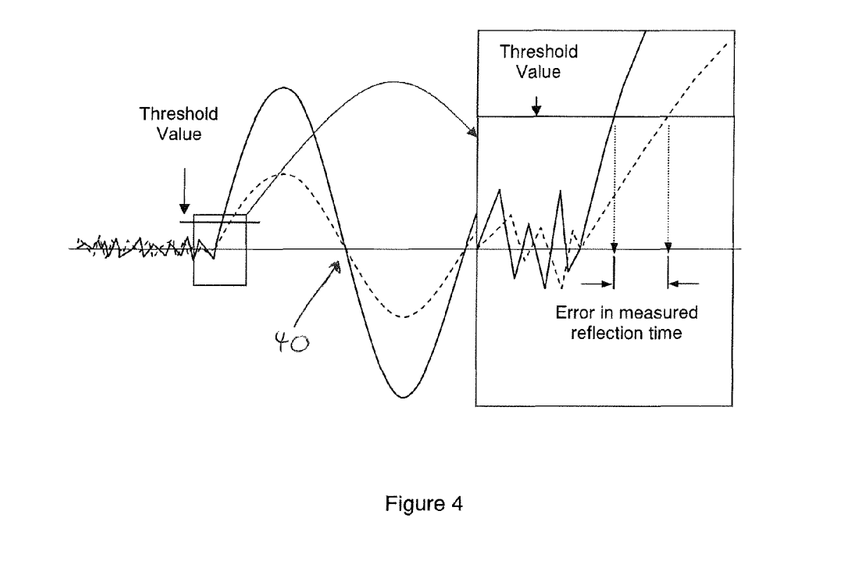
FIG. 4 illustrates two reflected signals of differing amplitudes.

A logical approach might be to look for the leading edge of the reflected wave. If a capacitor bank has been used to generate the initial pulse, it is typical that there is a delay in reaching the zero amplitude following the pulse emission, and this can impinge on the first reflection. This effect makes resolution of the time at which the reflection occurred 37 (i.e. the time which is equivalent to the start time 35 of the transmitted pulse) difficult. FIG. 3 illustrates how the start time 37 of the ideal (without noise) reflection can be obscured in detail 36. If the time of flight were measured to the apparent 'zero' 38 a time shift error is introduced. If an operational amplifier system is used, and there is no delay in reaching zero amplitude, there is still a problem in determining when the leading edge threshold value has been triggered. This is shown in FIG. 4, where the background noise of the signal makes identifying the zero amplitude point where the leading edge rises difficult.

Another difficulty in measuring between the origin times of the two pulses is that, in data analysis, when identifying a wave, typically a threshold value is looked for rather than the actual zero point itself. Because the amplitude of a reflection can change from wave to wave, this method can introduce further error, as illustrated in FIG. 4. In particular, it takes longer for a reflection having a lower peak amplitude (shown in broken lines) to reach the threshold value than another reflection having a higher peak amplitude (shown in solid lines), introducing an apparent difference in time of flight between the two waves, where none in fact exists.

Due to the noise which can obscure the leading edge of a reflected wave, instead time of fight is measured to an intercept zero 40. An intercept zero 40 is one at which the wave re-crosses the amplitude axis (i.e. has zero amplitude but a time after the start time of the pulse). The intercept point 40 used in the system described herein is the first intercept zero, or 'second zero', but subsequent intercept points could be used if desired.

At such an intercept point the wave is essentially linear, such that the location of the point can be interpolated repeatably from measurements made before and after crossing the axis with the least disturbances from other noise. This point is essentially unaffected by changes in the amplitude of the wave, as shown in FIGS. 3 and 4. At this point also, there are no "shoulders" within the signal from other frequencies which would again add errors.

When considering this linear interpolation between the actual measured values either side of the zero amplitude axis, the greater the frequency of signal, the steeper the gradient of the line and the smaller the error of measurement. However, as discussed above, the frequency selected for the signal needs to be balanced with other requirements of the system, particularly the depth of material through which the signal needs to be transmitted.

Figure 8:
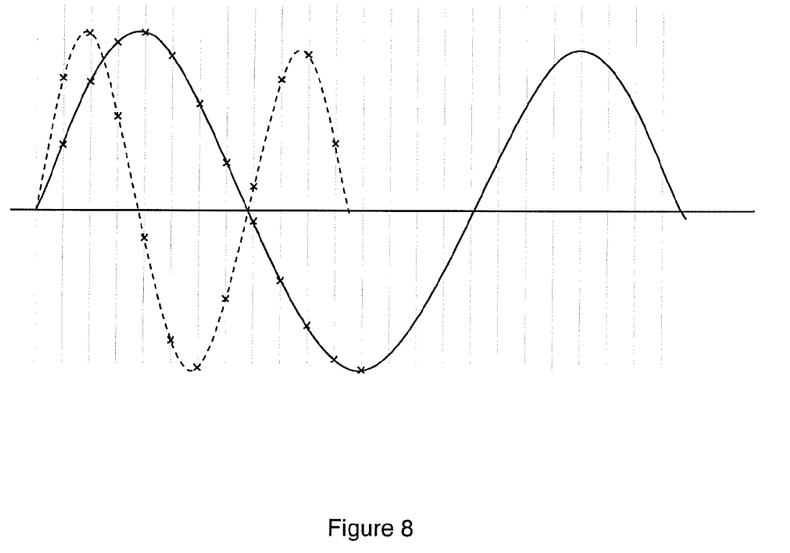
FIG. 8 illustrates two ultrasonic waves which have different frequencies but which are sampled at the same rate.

In addition, where a higher frequency is used, it may be necessary to increase the data sampling rate. FIG. 8 illustrates two ultrasonic waves which have different frequencies, but are sampled at the same rate. On the figure the dotted line represents the higher frequency signal, the solid line represents the lower frequency signal. When interpolating the intersection with the zero axis, although the gradient of the high frequency line is steeper there is less data representing the gradient. In this example the solid line represents a 10 MHz signal sampled at 100 MHz and the dotted line represents a 20 MHz signal sampled at 100 MHz.

When a signal is reflected from the test surface, a portion of that signal is reflected back towards the test surface from the surface to which the ultrasonic transducer is coupled. A portion of that re-reflected signal is then reflected again as a second reflection. Theoretically, measuring the time of flight of such a second reflection (or a higher order reflection, such as a third, fifth or even twentieth reflection) would produce a more accurate result due to the greater distance traveled by such a reflection.

However, selection of the order of reflection again has to be balanced against the quality of the reflected signal, and its ability to be reliably differentiated from the background noise. Through experimentation we have determined that whilst one would think it better to use a higher order reflection, the best measurement appears to be between the time at which the ultrasound was generated and the first reflection.

Statistical Analysis

As discussed above, there are a series of errors from a variety of sources, including background noise, which can affect the accuracy of the time of flight measurement. Some ways of reducing these errors were discussed above, but each individual measurement is nevertheless of limited accuracy due to the difficulty in measuring very short time periods.

To produce a less uncertain time of flight value, a series of measured values ('samples') are aggregated and statistical operations performed on them to determine a composite value for the thickness of the material. The more samples that are combined, the less uncertain the resulting composite value. The number of samples which can be taken is physically restricted, because of the necessity to wait until the first reflected signal has been received (and possibly further reflections have died away) before transmitting a second signal.

A suitable sample set might include between 10,000 and 80,000 samples taken at regular intervals over a 1 second period. The example system described below is operable to collect a sample set of approximately 40,000 samples every three seconds.

Calculating a mean (as opposed to median or mode) from a sample set of this size is computationally intensive. In particular, we have found that in terms of computational speed it is better to generate more small data sets and then undertake statistics upon them rather than statistics on a single larger data set. This is because small data sets can be processed in real time, whilst processing large data sets generally requires writing data and reading data, which slows down the calculation process. In one version of the system, a set comprising information derived from a plurality of received signals is broken down into a plurality (and in particular ten) smaller sub-sets. Each sub-set is averaged to product a time of flight 'sub-value', and the resultant sub-values are then combined to produce the composite value. This two-stage statistical analysis can be completed more quickly and efficiently than simply producing an average of the complete set of individual measured time of flight values. In addition, we have found that sampling continuously for 1 second is not as accurate as taking multiple sample sets over a 1 second periods (e.g. producing a sample set every 0.2 seconds). This is because the effects of temperature change are likely to be smaller over a shorter time.

Each sub-set might include a sample size with a range of 2-100,000 time of flight values, such as 2-45,000, 100-10,000 or 3000 to 5000. In the example system described below 4005 samples are taken in each sub-set. This number has been selected as the number of discrete samples which are taken in 0.2 s. In theory a larger number of smaller sub-sets might allow a composite value to determined more quickly. However, it is difficult to synchronously link sub-sets spanning a time period shorter than 0.2 s to temperature.

Thus in one example system ten sub-sets of 4005 are produced over ten consecutive 0.2 s periods (which might be 0.1 seconds apart). A time of flight sub-value is produced for each sub-set. Those ten sub-values are then combined to produce a time of flight values for a three second period. That composite time of flight value includes data from approximately 40,000 individual measurements.

An alternative approach to calculating a mean of each sub-set would be to interleave a sub-set of samples (e.g. up to 20 sequential samples might be interleaved) to generate a more accurate single wave. These interleaved waves could then be statistically combined as discussed above to produce the composite value.

Temperature Compensation

A change in temperature changes several properties of the measurement. These properties include amongst others:
Expansion/contraction of the material being measured thus changing the apparent thickness recorded
Changing the response characteristics of the ultrasonic transducer
Expansion/contraction of the glue-line
Changes to the speed of sound through the glue and measured material.
Changes in the speed of sound through the material.

The above effects are repeatable and to a large extent linear with temperature. Therefore it is possible to compensate for temperature changes when producing a dimensional value. This can be done using a first order correction based on an experimental calibration where no wear is taking place, but the temperature is being varied. By measuring a specimen subject to temperature change, but not wear, it is possible to relate temperature and thickness.

Figure 5:
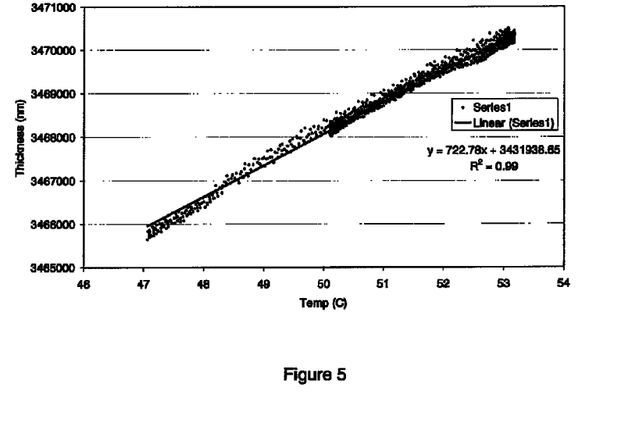
FIG. 5 illustrates the effects of temperature change on apparent thickness.

FIG. 5 shows the results of such a calibration. In the graph shown the data points were collected during an experiment where a specimen was heated and cooled but not subjected to wear. Each data point is the result of 4005 measurements of thickness captured in 0.2 seconds. The system was run at 100 collections per minute and the thickness plotted against temperature. From this point a linear relationship is assumed and an appropriate 'straight-line' function calculated (although other options are available, such as spline functions, look-up tables or polynomials). This relationship is then used to equate subsequent readings (e.g. during a wear test) to the original. For example, measured thickness might be calibrated back to a standard temperature.

Temperature variations can significantly alter the measured thickness values. Therefore it can be desirable to acquire accurate temperature measurements substantially simultaneously with the ultrasonic thickness measurements, allowing the dimensional value to be calibrated. One way of obtaining accurate and repeatable temperature readings is using a thermocouple mounted on the surface of the item under test next to the ultrasonic sensor. It may also be useful to provide additional temperature reading from other locations, e.g. on a remote surface of the item (e.g. the surface which is subjected to wear) or at another depth in the item.

Practical System

Figure 6:
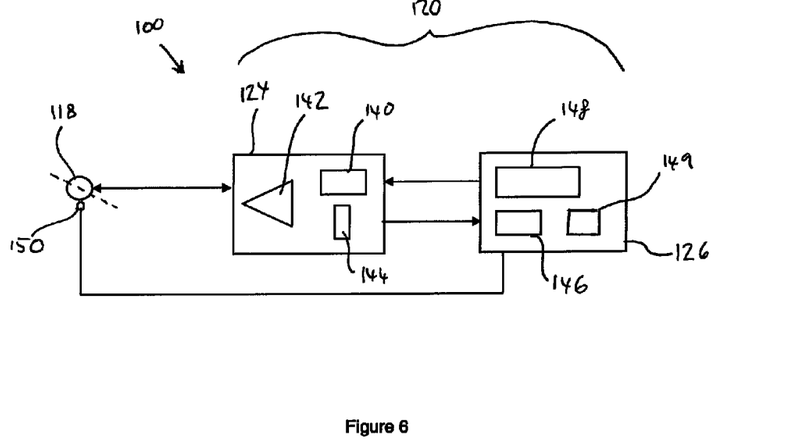
FIG. 6 schematically shows an alternative system for measuring a dimension of an item.

An ultrasonic dimension measuring system 100 which takes into account the above considerations is depicted schematically in FIG. 6. The system 100 shares many features in common with the apparatus 10. In particular the system 100 includes an ultrasonic transceiver 118, and a control system 120 including a pulse generation module 124 and a controller module 126.

The ultrasonic transducer 118 comprises a piezoelectric transducer which is fixed in use to an item under test (not shown) using a fixing such as glue. If desired, the ultrasonic transducer might be deposited in situ on the surface of the item. The fixing selected depends primarily on the item and the conditions it is expected to experience in use, but needs to enable good transmission of ultrasound signals over the temperature range expected in use. When fixed in place the sensor may be covered with a backing to assist in transmitting the ultrasonic signal to the item, such as an epoxy resin backing, for example steel reinforced epoxy. The transducer 118 has a frequency of approximately 10 MHz, although other frequencies are possible, as discussed above.

The pulse generation module 124 is operable to generate a voltage pulse having a peak amplitude of approximately 10V. The pulse generation module includes a pulse generator 140, an amplifier 142 and a signal blocker 144. The pulse generator is operable to generate a voltage pulse of substantially 1V which has a repeatable shape. In this example the pulse comprises a sine wave with a frequency of substantially 10 MHz, and the pulse generator 140 comprises a first programmable element such as a field programmable gate array (FPGA 1). As well as generating the initial pulse to be transmitted, the FPGA 1 is operable to receive the reflected signal.

The amplifier 142 is operable to amplify the shaped signal produced by the FPGA 1 to approximately a 10V pulse without altering the frequency. If such a high voltage signal were received by the FPGA 1, then it would damage the FPGA 1. Therefore, when the amplifier is active the signal blocker 144, which in this example is a field-effect transistor (FET), is activated simultaneously to ensure that no portion of the 10V signal can be transmitted back towards the FPGA 1. As soon as the amplifier has transmitted the 10V pulse, the signal blocker 144 is deactivated to allow the reflected signal to be detected by the FPGA 1.

The controller module 126 includes a further programmable element 146 such as a second field programmable gate array (FPGA 2) and a processor 148, and a memory 149. The FPGA 2 is operable to collect temperature data from temperature sensors 150, such as thermocouples, arranged to measure the temperature of the item under test.

The processor 148 is in signal communication with both programmable elements 140 and 146, and receives signal data from FPGA 1 and temperature data from FPGA 2. The processor uses the received signal data and temperature data to produce a dimensional measurement.

In operation, the system 100 performs the following two sets of operations substantially simultaneously under control of the processor.

Firstly, programmable element 140 generates a 1V pulse 50 ns in duration. The signal blocker 144 is activated, and the amplifier 142 amplifies the 1V pulse to 10V. The signal blocker is then deactivated. The 10V signal is transmitted to the ultrasonic transceiver 118 over a cable. The ultrasonic transceiver converts the signal to an ultrasonic pulse, and transmits the pulse into the item under test. A reflected ultrasonic pulse is subsequently received by the ultrasonic transceiver, converted to an electrical signal, and detected by the programmable element 140. Data identifying the received signal (and in particular a collection of discrete measurements which together are indicative of the shape of the received signal) is transmitted to the processor for analysis/storage, and in particular for generation of a time of flight value. This set of operations is repeated a predetermined number of times in a specified time period, and in this example is repeated approximately 4005 times in 0.2 s.

The ultrasonic transceiver 118 may be replaced by an ultrasonic transmitter and an ultrasonic receiver embodied separately. This will help to isolate the receiver from the excitation provided by the transmitter, to render the signal blocker 144 unnecessary. This is indicated in FIG. 6 by a broken line through the transceiver 118 to indicate the use of a transmitter and a separate receiver.

Simultaneous with the above collection of time of flight data, the processor instructs the second programmable element 146 to collect temperature data from the temperature sensor 150. A measured temperature value (which consists of two measurements) is stored in memory until FPGA 1 has collected the predetermined number of samples. These operations are arranged to start and finish substantially synchronously.

Once the signal data for the predetermined number of measurements has been collected, the processor determines a time of flight for each measurement by locating the first intercept zero, as discussed above. The set of time of flight values are then averaged to produce a single time of flight value, which is calibrated using the temperature value. A temperature independent dimensional value is then calculated. That value is indicative of the thickness of the item under test in the 0.2 s over which the measurement operations took place.

The system is operable to repeat the above operations a predetermined number of times to produce further dimensional values, which can then be combined to produce a more accurate composite dimensional value averaged over a longer time period (e.g. 1 s). In particular, the system is arranged to repeat the above operations ten times (for example at intervals of approximately 0.5 seconds), and to average the resulting ten dimensional values to produce a composite dimensional value for a 5 second period.

The entire method (including the second averaging step) can be repeated as many times as desired. For example, the method might be repeated at regular intervals, for example every minute, or every ten minutes, to produce a plurality of composite dimensional values. A record of such composite dimensional values, and perhaps their respective times of measurement, may be stored (either in memory 149 or in another, possibly remote, location), to produce a record showing change in dimension (if any) over time.

The above system and method can be used to measure dimension in a range of materials such as metal, plastics or composites, and the material properties and thickness will affect the signal quality being generated. Typically the system is able to measure changes in dimension of items with initial dimensions ranging between 3-400 mm or 3-300 mm, more typically 3-100, or 3-30 mm, depending on material properties.

The system can operate under a range of conditions, and in particular is not limited to use in a laboratory. For example, the system might be installed in a machine under test, which might be a vehicle such as an automotive vehicle or a nautical vessel, and used to produce real time measurements of dimension whilst the vehicle is in use.

The system might include multiple ultrasonic transducers, allowing multiple components in the same vehicle to be measured simultaneously. In such a system, each ultrasonic transducer would comprise a respective temperature sensing arrangement, but might share a single processor and single pulse generator.

The control system might be in communication (for example wireless communication) with a remote control hub. Dimensional measurements, along with other measured data such as time and temperature data, might be transmitted to the control hub by the control system using a wireless transmission device. The data acquired by the system can thus be analysed in substantially real time from a remote location.

Various other modifications may be made without departing from the scope of the invention. For example, different means of pulse generation might be used, and different methods of temperature measurement might be used. It will be understood that the diagrams shown in FIGS. 1 and 6 are illustrative only, and not necessarily indicative of the physical locations of the components mentioned. In particular, the first programmable element 140 might be comprised with a housing including the second programmable element 146, which might be separate from a housing including the amplifier and signal blocker. The processor 148 might be comprised in the same housing as the programmable element, or might be remote from the remainder of the system.

It will be appreciated that the method steps might be conducted in any suitable order, and in particular that the step of statistically combining the signals might take place at any suitable stage of the method. As described above with respect to FIG. 6, the signal information is combined after time of flight values have been produced for each received signal. It will be appreciated that instead the time of flight data representing the received electrical signals might be combined prior to producing a composite time of flight value from that combined date. Alternatively, a plurality of individual dimensional values might be produced, one for each reflected signal, or sub-set of reflected signals. Those dimensional values might then be statistically combined to produce the composite dimensional value.

It will be appreciated that the voltages, frequencies and sample set sizes which are appropriate may vary depending on the type of material under test, the thickness of the material, the type of sensor and the temperature of operation. The system described above with respect to FIG. 6 was optimised for use with a metal such as steel. However, other materials might require larger or smaller sample sizes, higher or lower voltages, and higher or lower frequencies than those discussed. Furthermore, other materials may not be affected significantly by temperature changes, such that temperature calibration may not always be necessary.

Whilst endeavouring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

What is claimed is:

1. A method of ultrasonic measurement to determine the effect of wear, the method comprising the steps of:
   transmitting an ultrasonic signal into an item which is subject to wear,
   receiving an ultrasonic signal from the item, the received signal comprising a reflection of the transmitted signal from a boundary of the item,
   repeating the transmitting and receiving steps a plurality of times in a specified period,
   extracting from each received signal information indicative of a dimension of the item, and determining a time of flight value from the information extracted from a respective received ultrasonic signal, and
   combining the plurality of time of flight values extracted from the plurality of received signals to produce a composite time of flight value indicative of the dimension of the item over the specified period, wherein producing the composite time of flight value comprises performing a statistical operation.

2. A method according to claim 1 wherein a set comprising a plurality of time of flight values is produced, each time of flight value in the set corresponding to a respective received signal.

3. A method according to claim 1, wherein the statistical operation comprises taking an average of the time of flight values.

4. A method according to claim 1, wherein producing the composite time of flight value comprises the step of producing a plurality of time of flight sub-values, and combining the time of flight sub-values to produce the composite time of flight value.

5. A method according to claim 1, wherein producing the value for dimension comprises producing a composite time of flight value from the information extracted from the plurality of received signals, the composite time of flight value being indicative of an average time of flight, and using the composite time of flight value to determine the value for the dimension of the item.

6. A method according to claim 1, wherein the transmitting and receiving steps are repeated between 1000 and 100,000 times over the specified period.

7. A method according to claim 1, wherein the transmitting and receiving steps are repeated 4005 times over a period of 0.2 seconds.

8. A method according to claim 1, wherein the item comprises a material selected from the group comprising: metals, alloys, plastics, concrete, ceramics, coated materials, coatings, composite materials, steel, aluminium, copper, brass, tin, lead, bismuth, aluminium oxide and aluminium silicate.

9. A method according to claim 1, wherein the step of determining the time of flight value comprises identifying a time at which a zero amplitude of the reflected signal occurred.

10. A method according to claim 1, wherein the receiving step comprises receiving a first reflection of the transmitted signal.

11. A method according to claim 1, wherein the receiving step comprises receiving a higher order reflection.

12. An apparatus for ultrasonic measurement to determine the effect of wear, comprising:
    an ultrasonic transmitter operable to transmit an ultrasonic signal into an item, which is subject to wear;
    an ultrasonic receiver operable to receive an ultrasonic signal from the item, the received signal comprising a reflection of the transmitted signal from a boundary of the item;
    the transmitter and receiver being operable to transmit and receive a plurality of times in a specified period,
    the receiver being operable to extract from each received signal information indicative of a dimension of the item, and to determine a time of flight value from the information extracted from a respective received ultrasonic signal, and
    the receiver being operable to combine the plurality of time of flight values extracted from the plurality of received signals to produce a composite time of flight value indicative of the dimension of the item over the specified period, and to perform a statistical operation to produce the composite time of flight value.

13. An apparatus according to claim 12 comprising an ultrasonic transmitter operable to transmit an ultrasonic signal into an item and an ultrasonic receiver operable to receive an ultrasonic signal from an item.

14. An apparatus according to claim 12 comprising an ultrasonic transceiver providing the ultrasonic transmitter and the ultrasonic receiver.

15. An apparatus according to claim 14, wherein the apparatus comprises a control system which is operable to supply an electrical signal to the ultrasonic transceiver to cause the ultrasonic transceiver to transmit the ultrasonic signal.

16. An apparatus according to claim 15, wherein the control system is operable to cause the ultrasonic transceiver to transmit a plurality of ultrasonic signals in a specified period.

17. An apparatus according to claim 16, wherein the control system is operable to supply a voltage pulse to the ultrasonic transceiver.

18. An apparatus according to claim 17, wherein the pulse generation module is operable to shape the voltage pulse.

19. An apparatus according to claim 18, wherein the voltage pulse generation module is operable to produce a square wave, a triangle wave, or a sine wave or other shaped wave.

20. An apparatus according to claim 19, wherein the pulse generation module is operable to produce waves at frequencies between 1 and 100 MHz.

* * * * *